(12) United States Patent
Vilsmeier et al.

(10) Patent No.: US 6,609,022 B2
(45) Date of Patent: Aug. 19, 2003

(54) INTRAOPERATIVE NAVIGATION UPDATING

(75) Inventors: Stefan Vilsmeier, Kufstein (AT); Akos Dombay, HöhenKirchen (DE)

(73) Assignee: BrainLAB AG, Kirchheim/Heimstetten (DE)

( * ) Notice: Subject to any disclaimer, the term of this patent is extended or adjusted under 35 U.S.C. 154(b) by 127 days.

(21) Appl. No.: 09/756,582

(22) Filed: Jan. 8, 2001

(65) Prior Publication Data

US 2001/0007918 A1 Jul. 12, 2001

(30) Foreign Application Priority Data

Jan. 12, 2000 (DE) .......................... 100 00 937

(51) Int. Cl.⁷ ................................ A61B 5/05
(52) U.S. Cl. ...................................... 600/426
(58) Field of Search .................. 600/426, 425, 600/424, 407; 378/21; 250/363.01; 606/2, 20, 27, 32

(56) References Cited

U.S. PATENT DOCUMENTS 5,851,183 A * 12/1998 Bucholz ................. 600/424
6,052,477 A * 4/2000 Wang et al. ............. 378/162
6,122,541 A * 9/2000 Cosman et al. .......... 600/426
6,246,784 B1 * 6/2001 Summers et al. ......... 382/128
6,246,900 B1 * 6/2001 Cosman et al. .......... 600/426
6,259,942 B1 * 7/2001 Westermann et al. ..... 378/162
6,381,485 B1 * 4/2002 Hunter et al. ........... 324/244

FOREIGN PATENT DOCUMENTS

DE 198 46 687 A1 4/2000

* cited by examiner

Primary Examiner—Teresa Welberg
Assistant Examiner—Daniel Robinson
(74) Attorney, Agent, or Firm—Renner, Otto, Boisselle & Sklar, LLP

(57) ABSTRACT

The invention relates to a method for supporting the treatment of a patient, of which a patient data record was made available by an image-generating method, by means of a navigation system, the navigation system detecting and tracking the positions of the patient, of his/her parts of the body, and particularly of the target of the treatment and the treatment devices, wherein, either automatically or on demand, either one or several further current patient data records are created by means of an image-generating method, and wherein each current data record is integrated into the navigation system in a computer-aided manner.

8 Claims, 1 Drawing Sheet

INTRAOPERATIVE NAVIGATION UPDATING

BACKGROUND OF THE INVENTION

TECHNICAL FIELD

Figure 1:
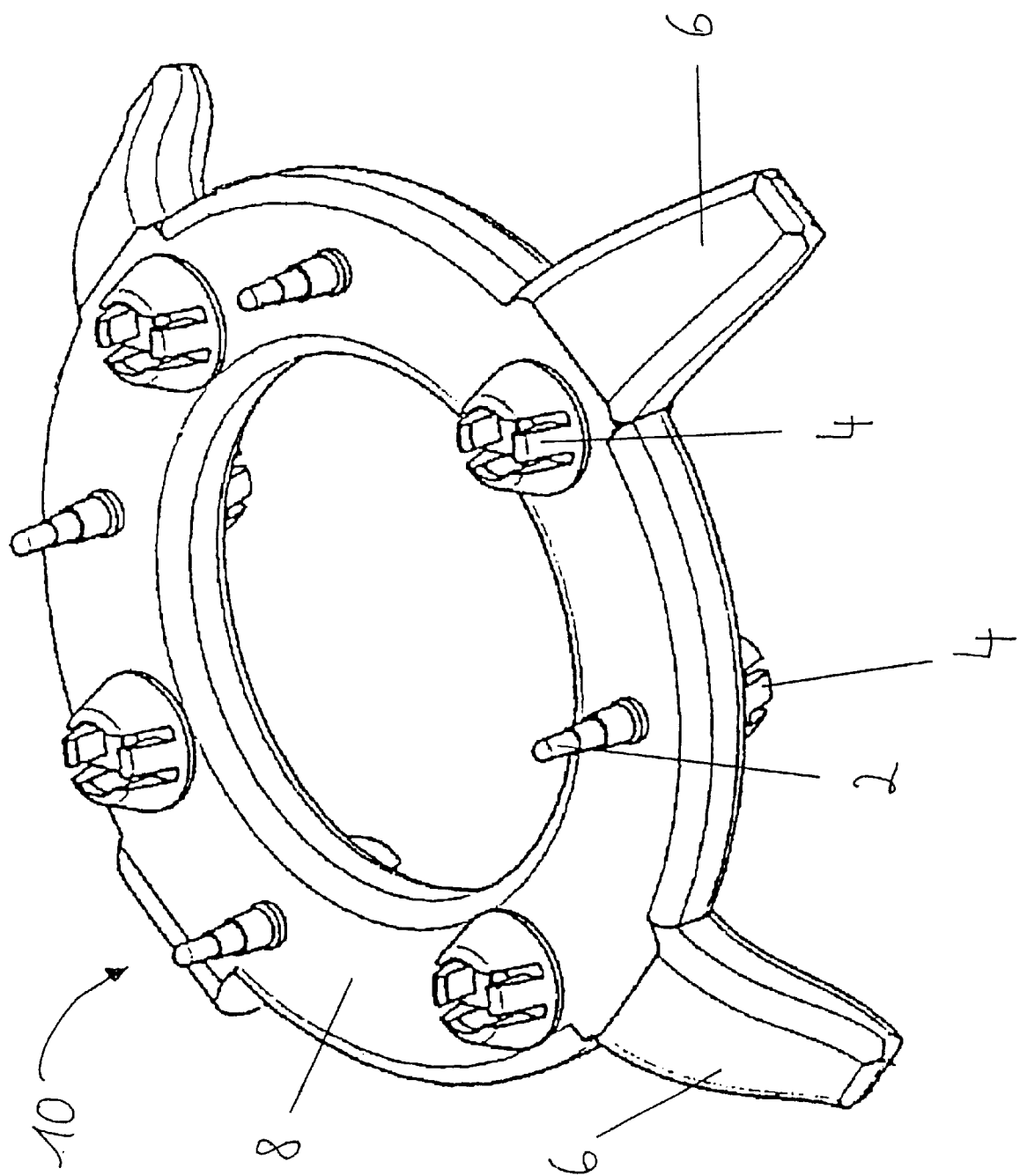

The present invention relates to a method for supporting the treatment of a patient by means of a navigation system. Such navigation systems detect and track the positions of patients, parts of the patient's body, and targets of treatment as well as of treatment devices, and show, in many cases, the surgeon concerned images on a monitor, which he uses to support his treatment.

In this connection, problems may arise in the course of treatment if the tissue is subjected to shifting during treatment, as may happen, for example, due to liquid discharge or removal of tissue. In such a situation, i.e. if the target of treatment or the surrounding tissue together with the target of treatment has been shifted, the supporting navigation becomes inaccurate, with the result that the surgeon involved is again entirely left to his own observations or, if he did not notice the shift, might possibly operate at wrong positions.

SUMMARY OF THE INVENTION

It is therefore an object of the present invention to provide the treating surgeon with a means enabling him to still navigate precisely by means of a navigation system even after tissue has been shifted during an operation.

According to the invention, this object is solved by a method as set forth in claim 1. Advantageous embodiments of the inventive method are described in the sub-claims.

The advantages of the method in accordance with the invention are particularly based on the fact that, in addition to the data record the navigation system has used up to that moment, one or several further current patient data records are created, either automatically or on demand, by an image-generating method, and that each current data record is integrated into the navigation system in a computer-aided manner. It is, thus, not only ensured that a new and current data record, recording the cited tissue shifts and changes, is available at a given time, but the current data record will simultaneously be linked or integrated into the navigation system so that the surgeon concerned is able to continue his work quickly with the assistance of a precisely integrated and updated navigation support. Accordingly, incorrect treatment can be avoided, and the surgeon concerned no longer has to depend on visually perceiving large-scale tissue removals or liquid discharges.

The other data record/s of the patient can be created during the operation by means of different methods. These are, in particular, magnetic resonance tomography (MR), computer tomography or the SPECT or PET methods.

In a first specific embodiment of the method according to the invention, a reference structure is positioned at the patient or in the surrounding area of the target of treatment while the current data record is being created, said reference structure comprising markers which can be detected by the navigation system as well as markers which can be detected by the image-generating method, the assignment of data for the markers resulting in a positional integration of the current data record into the navigation system. According to another, but similar, embodiment, the reference structure comprises markers detectable in the navigation system as well as by the image-generating method.

Accordingly, the reference structure and the markers thereof are the point of intersection for the assignment of the current data record into the navigation system. Due to the positional detection of the navigation system marker, the navigation system knows the position of the reference structure and, furthermore, its position is known in the newly created data record, as here markers are also detected at the reference structure. Similarly, the image-generating system also knows the position of the pixels and can detect/compensate the deviations between the individual data records of the patient (caused by different positions of the patient) and/or transmit them to the navigation system. Thus, each subsequently following data record is automatically referenced, i.e. only the first data record has to be localized/referenced, provided that the patient is firmly fixed, e.g. by means of a rigid head fixation.

According to another specific embodiment of the inventive method, the new data record can be integrated into the navigation system in that the current data record is assigned, as concerns the position, to the data record to be updated by means of a computer-aided, automatic, three-dimensional image fusion, referencing of the current data record occurring in the navigation system from the computed positional shift. Both data records, i.e. the one already available in the navigation system and the current data record from the image-generating device, which both supply three-dimensional image data, may be brought into conformity with each other by means of what is known as image fusion by a suitable computer program. If this could have been reached with sufficient conformity, one can gather from this that one transformation that leads from the data record to be updated to the current data record, and by means of such a transformation, the neuro-navigation system may be set anew and to the current state and the current positioning of the tissue to be treated. This method is especially advantageous as no further means are required; updating can be done on demand, e.g. by pressing a button. Similarly, the above-described image fusion can, of course, also be started automatically without any user actions being required.

With regard to the above-referenced method, it is possible to proceed in such a manner that the image fusion is, at least partially, solely based on those data record elements from the current data record and the data record to be updated, which do not reflect any, or just a restricted, deformation of the detected part of the body. This option is especially useful to reduce computing times and to avoid larger errors if rigid transformations, as will be described later, cannot supply valid results any more.

DETAILED DESCRIPTION OF PREFERRED EMBODIMENTS

In the case of preferred embodiments of the method in accordance with the invention, the image fusion may include one or several of the following features:

- it is based on a rigid transformation;
- it is based on a search region consisting of all rigid transformations (rotation, translation) between the data records;
- it is searched for that transformation in the search region that brings the data records into conformity;
- the quality of transformations is measured with regard to a criterion of conformity that is computed from the correlation of intensity of a great number of corresponding pixels in both data records;
- the suitable transformation is determined by solving an optimization problem looking for a transformation parameter record for which the criterion of conformity reaches a maximum value;

the suitable transformation is determined stepwise by using more and more image data in the later steps so as to improve conformity in an iterative manner;

as few as possible determinations of the criterion of conformity are performed.

Such an automatic image fusion module can be used to bring three-dimensional medical data records into conformity. It operates under different methods (CT, MR, PET, SPECT . . . ) and independent of the scanning direction of the respective image data records. The image data records can be partial data records if the overlap region is of sufficient size. In detail:

A rigid transformation from one image data record to the other is computed by the automatic image fusion to bring the image data records into conformity with each other. It is particularly suitable for the fusion of images of one and the same patient.

Any distortions in MR (magnetic resonance tomography) images are not crucial, as they mostly occur in the outer regions of the images. Automatic image fusion is based on the undistorted central regions.

As mentioned, image fusion is based on a search region consisting of all rigid transformations of an image data record in relation to the other image data record. Each rigid transformation is described by its degree of translation and rotation. It is the task of automatic image fusion to find those transformations in the search region which bring the image data records into conformity.

Automatic image fusion uses a criterion of conformity to evaluate the quality of a specific translation and rotation. This criterion operates for any statistic relations of the image intensities (the same kind of tissue may include greatly differentiating intensities in one image date record as compared to another image data record).

The criterion of conformity is computed by establishing the intensity values of a greater number of pixels and comparing them to the corresponding pixels in another image data record.

Determination of the suitable transformation can be formulated as an optimizing problem as follows: Find a set of transformation parameters with a maximum criterion of conformity.

The algorithm is executed in different steps. Each step uses more subtle details to compute the criterion of conformity than did the preceding one. The first step uses little image data, thus making optimization fast and robust. The following steps improve the conformity in an iterative manner by processing more and more of the image data.

The optimizing algorithm used to find the maximum value for the criterion of conformity and the appertaining transformation parameter is very highly developed. As the interpretation of the criterion of conformity is very time-consuming, a search strategy may be implemented that uses as little interpretations as possible.

The following describes another specific embodiment of the method in accordance with the invention. In this embodiment, the device for performing the image-generating method is referenced by the navigation system while the current data record is being detected by means of the markers provided thereon, which may be detected by said navigation system, and the position of the current data record, is thus integrated. This method is similar to the embodiment described first, the markers, however, not being attached to the patient or near the patient, but directly to the device for performing the image-generating method, i.e., for example, directly to a mobile MR device which is brought into the operational theater to update data records.

Briefly, in this embodiment the navigation system knows from the markers where the device for performing the image-generating method is positioned in the region at the moment the new images are being created, thus allowing to compute back to the position of the new images per se.

Sometimes, such a positional determination may become difficult, i.e. in the case when the position in the region where the new image is just being created has not yet precisely been known already in relation to the device for performing the image-generating method. However, such relative positions can be detected by trial-and-error, and, according to another embodiment of the present invention, a specific given detection of coordinates can be done by which the relative position of the current data record is determined with regard to the device for performing the image-generating method.

The invention will now be explained in detail by means of an embodiment.

The enclosed FIGURE shows a reference structure as it can be used to integrate the position of an updated data record into a navigation system. The reference structure is given reference number 10. It comprises a carrier ring 8 with arms 6. Said carrier ring 8 includes markers, for example infrared-reflecting markers (IR markers) 2 as well as fixtures 4 for MR markers (not shown), which are visible in a magnetic resonance tomographic image. These fixtures are provided on both the top and the bottom side of said ring 8 to receive ball-shaped MR markers therein. It can be assumed that all conceivable tracking systems can be used within the scope of the present invention, i.e. for example also those comprising actively radiating markers, magnetic systems or systems based on ultrasonics. MR-visible markers of different shape may also be used, e.g. flat or cornered markers.

The use of such a reference structure will now be explained in detail with regard to the course of a treatment using navigation updating according to the invention.

First of all, a diagnostic image data record of a patient is created, e.g. a computer tomography data record. Then, the patient is moved into the operating theater where, in advance, the first data record may again be adjusted by means of known adjusting methods so as to make a correctly referenced initial data record available for navigation.

Now, the surgeon concerned performs the image-guided operation with the assistance of the navigation system. Should the surgeon find out in the course of the operation that a great amount of tissue liquid has already been drained off or that tissue has already been removed to such an amount that inaccuracies occur in the navigation system due to the shift of tissue, he can activate the intra-operative navigation updating in accordance with the present invention. To do so, the patient is, first of all, covered with sterile cloth. If the operation is to be performed in the region of the head, a sterilized reference structure 10 can be placed, for example, on the patient's face, and the generation of the current data record be started. To do so, a mobile MR device, for example, is moved into the operating theater and positioned beside the patient's head. All treatment devices that are not MR-compatible, instrument trays and other equipment such as surgical microscopes should be positioned at a safe distance away from the MR device.

In the case of the intra-operative MR scan, the IR markers 2 and the MR markers of fixtures 4 are also scanned or detected by the navigation system, and the position of the new updated image data can be integrated into the navigation system in computer-aided manner by means of the reference structure used as point of intersection between said two detecting systems. Accordingly, after such a MR scan, the updated data are made available to the navigation system, and the surgeon is again able to operate with the help of a precise image assistance as soon as the reference structure and the sterile cloth have been removed from the patient.

As the MR scanner is moved and the patient remains in his/her position, the operation is interrupted for some minutes only.

In this connection, it is also possible to create a postoperative data record for checking purposes. To do so, the MR scanner is again moved into the operating theater while the patient is still anaesthetized and intubated. The data record, which will then be created anew, is pictorially represented and can be immediately checked by the surgery team. Such a final check-up is an important aid used to confirm that a complete tumor resection has taken place and to exclude acute complications, thereby considerably reducing the risk of having to perform a further operation in case the tumor should grow again. This also helps to reduce costs arising from repeated operations.

In the foregoing description, preferred embodiments of the invention have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

What is claimed is:

1. A method for supporting comprising the steps of:
   providing a first patient image data record;
   integrating the first patient image data record into a navigation system through a computer-aided process;
   using said navigation system to detect and track the positions of the patient and at least one treatment device;
   generating at least one current patient image data record by means of an image-generating method; and
   integrating the current patent image data record into the navigation system in a computer-aided manner by performing image fusion of the current patient image data record with the first patient image data record.

2. The method as set forth in claim 1, wherein the current patient data record is created by a method selected from the group consisting of magnetic resonance tomography (MR), computer tomography (CT), SPECT and PET.

3. The method as set forth in claim 1, wherein the step of generating at least one current patient image data record comprises locating at the patient a reference structure having a known arrangement of markers which can be detected by the navigation system and by a device that generates the patient image data record; and using the known arrangement of markers to effect positional integration of the current patient data record in the navigation system.

4. The method as set forth in claim 3, wherein the reference structure comprises at last one that can be detected by both the navigation system and by the device that generates the current patient image data record.

5. The method as set forth in claim 1, wherein the image fusion is solely based on those data record elements from the current data record and from the patient data record to be updated that reflect no deformation or restricted deformation of a detected part of the patient's body.

6. The method as set forth in claim 1, wherein the image fusion is characterized by at least one of the following features:
   it is based on a rigid transformation;
   it is based on a search region consisting essentially of rotation and translation rigid transformations between two data records;
   transformations in the search region are used to bring data records into conformity with each other;
   the quality of transformations is measured with regard to a criterion of conformity;
   a criterion of conformity is computed from a correlation of intensity of a plurality of corresponding pixels in the data records;
   a suitable transformation is determined by optimizing data records so that a criterion of conformity reaches maximum value;
   a suitable transformation is determined iteratively to improve conformity; and
   as few determinations of a criterion of conformity as possible are performed.

7. The method as set forth in one of claim 1, wherein the device that generates the current patient image data record is referenced by the navigation system during image data record generation.

8. The method as set forth in claim 7, wherein the relative position of the current patient image data record is determined with reference to the device that generates the patient image data record by detecting coordinates.

* * * * *